(12) United States Patent
Liu et al.

(10) Patent No.: US 9,776,942 B2
(45) Date of Patent: *Oct. 3, 2017

(54) PROCESSES FOR PRODUCING AN ACETIC ACID PRODUCT HAVING LOW BUTYL ACETATE CONTENT

(71) Applicant: Celanese International Corporation, Irving, TX (US)

(72) Inventors: Yaw-Hwa Liu, Missouri City, TX (US); Mark O. Scates, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 1 day.

This patent is subject to a terminal disclaimer.

(21) Appl. No.: 15/042,588

(22) Filed: Feb. 12, 2016

(65) Prior Publication Data

US 2016/0159721 A1 Jun. 9, 2016

Related U.S. Application Data

(63) Continuation of application No. 14/694,932, filed on Apr. 23, 2015, now Pat. No. 9,260,369.

(60) Provisional application No. 62/079,991, filed on Nov. 14, 2014.

(51) Int. Cl.
C07C 51/12 (2006.01)
C07C 51/44 (2006.01)

(52) U.S. Cl.
CPC .............. *C07C 51/12* (2013.01); *C07C 51/44* (2013.01)

(58) Field of Classification Search
CPC .................................................... C07C 51/12
See application file for complete search history.

(56) References Cited

U.S. PATENT DOCUMENTS

| | | | |
|---|---|---|---|
| 4,609,504 A | 9/1986 | Gauthier-Lafaye et al. | |
| 4,733,006 A | 3/1988 | Singleton et al. | |
| 4,792,620 A | 12/1988 | Paulik et al. | |
| 5,625,095 A | 4/1997 | Miura et al. | |
| 5,731,252 A | 3/1998 | Warner et al. | |
| 5,756,836 A | 5/1998 | Shimizu et al. | |
| 6,066,762 A | 5/2000 | Yoneda et al. | |
| 6,303,813 B1 * | 10/2001 | Scates ...................... | C07C 51/12 562/517 |
| 6,573,403 B1 | 6/2003 | Joensen | |
| 7,683,212 B2 | 3/2010 | Kojima et al. | |
| 7,855,306 B2 | 12/2010 | Zinobile et al. | |
| 9,260,369 B1 | 2/2016 | Liu et al. | |
| 2002/0151746 A1 | 10/2002 | Scates et al. | |
| 2013/0116470 A1 | 5/2013 | Miura et al. | |
| 2013/0261334 A1 | 10/2013 | Shimizu et al. | |
| 2013/0264186 A1 | 10/2013 | Shimizu et al. | |
| 2013/0281735 A1 | 10/2013 | Shimizu et al. | |
| 2013/0303800 A1 | 11/2013 | Shimizu et al. | |
| 2013/0310603 A1 | 11/2013 | Shimizu et al. | |

FOREIGN PATENT DOCUMENTS

| | | |
|---|---|---|
| EP | 0487284 | 5/1992 |
| JP | H04266843 | 9/1992 |
| JP | H10231267 A | 9/1998 |
| JP | 3244350 | 1/2002 |
| JP | 3244351 | 1/2002 |
| WO | 2008153708 | 12/2008 |
| WO | 2013137236 | 9/2013 |
| WO | 2014115826 | 7/2014 |

OTHER PUBLICATIONS

Japanese Office Action received in the corresponding Patent Application No. 2015-222664, dated Mar. 11, 2016.
Japanese Office Action received in the corresponding Patent Application No. 2015-101746, Appeal No. 2016-004542, dated Jan. 19, 2017, 32 pgs.
Third Party Observation received in the corresponding International Patent Application No. PCT/US2015/053843, dated Mar. 13, 2017.
Citation #5 from the Third Party Observation received in PCT/US2015/053843, dated Mar. 13, 2017 Title—"Control of propionic acid content in acetic acid production by carbonylation of methanol", dated Aug. 25, 2013, 20, pp. 50-52, p. 51, right column, line 4-13.
Citation #6 from the Third Party Observation received in PCT/US2015/053843, submitted Mar. 13, 2017 Title—"Control of formation of ethanol in methanol", dated Sep. 15, 2007, $5^{th}$ period, pp. 21-22, left column, lines 8-16.
Citation #7 from the Third Party Observation received in PCT/US2015/053843, submitted Mar. 13, 2017 Title—"A method to reduce ethanol content in purified methanol", dated Aug. 25, 2010, vol. 33, No. 4, pp. 225-227, p. 225, left column, line 2-9.
Citation #8 from the Third Party Observation received in PCT/US2015/053843, dated Mar. 13, 2017 Title—"Purification of crude methanol", Jan. 15, 1997, 1997, $1^{st}$ period, pp. 1-5 and 11, p. 2, left column, line 24—right column, line 3.
Citation #9 from the Third Party Observation received in PCT/US2015/053843, dated Mar. 13, 2017 Kirk-Othrner Encyclopedia of Chemical Technology $4^{th}$ Ed, Mass Transfer to Neuroregulators, A Wiley-Interscience publication; John Wiley & Sons, Inc., vol. 16, 1995, p. 554, lines 9-17.

(Continued)

*Primary Examiner* — Paul A Zucker
(74) *Attorney, Agent, or Firm* — Kilpatrick Townsend & Stockton LLP

(57) ABSTRACT

A process for producing an acetic acid product having low butyl acetate content via a carbonylation reaction. The carbonylation reaction is carried out at a temperature from 100 to 300° C., a hydrogen partial pressure from 0.3 to 2 atm, and a metal catalyst concentration from 100 to 3000 wppm, based on the weight of the reaction medium. The butyl acetate concentration in the acetic acid product may be controlled by removing acetaldehyde from a stream derived from the reaction medium and/or by adjusting at least one of reaction temperature, hydrogen partial pressure, and metal catalyst concentration.

6 Claims, 5 Drawing Sheets

(56) References Cited

OTHER PUBLICATIONS

Citation #10 from the Third Party Observation received in PCT/US2015/053843, dated Mar. 13, 2017 IMPCA Methanol Reference Specifications, International Methanol Producers & Consumers Association, Dec. 9, 2010, p. 1.
Title: "Specification of ethanol content of methanol products", May 15, 2008, 2008, $3^{rd}$ period, pp. 52-54, p. 53, left column, lines 14-20.
Title: "Consideration for four-column distillation process for methanol production", Sep. 20, 1998, 1998, $9^{th}$ period, pp. 21-22.
Haynes, Acetic Acid Synthesis by Catalytic Carbonylation of Methanol, Catalytic Carbonylation Reactions, vol. 18, 2006, pp. 179-205.
Japanese Application No. 2015-101746, Office Action dated Aug. 10, 2015, 12 pages, with English Translation.
International Application No. PCT/US2015/053843, International Search Report and Written Opinion dated Jan. 21, 2016, 11 pages.

\* cited by examiner

PROCESSES FOR PRODUCING AN ACETIC ACID PRODUCT HAVING LOW BUTYL ACETATE CONTENT

This application is a continuation of U.S. application Ser. No. 14/694,932, filed on Apr. 23, 2015, now U.S. Pat. No. 9,260,369, which claims priority to U.S. Provisional App. No. 62/079,991, filed on Nov. 14, 2014, the entirety of which is incorporated herein by reference.

CROSS-REFERENCES TO RELATED APPLICATIONS

This patent application claims priority from U.S. Provisional Patent Application Ser. No. 62/079,991, entitled "Processes For Producing An Acetic Acid Product Having Low Butyl Acetate Content", filed Nov. 14, 2014, the disclosure of which is incorporated herein by reference in its entirety.

FIELD OF THE INVENTION

This invention relates to processes for producing acetic acid and, in particular, to processes for producing an acetic acid product having low butyl acetate content.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, herein incorporated by reference. The carbonylation catalyst contains a metal catalyst, such as rhodium, which is either dissolved or otherwise dispersed in a liquid reaction medium or supported on an inert solid, along with a halogen-containing catalyst promoter as exemplified by methyl iodide. The rhodium can be introduced into the reaction system in many forms. Likewise, because the nature of the halide promoter is not generally critical, a large number of suitable promoters, most of which are organic iodides, may be used. Most typically and usefully, the reaction is conducted by continuously bubbling carbon monoxide gas through a liquid reaction medium in which the catalyst is dissolved.

During the carbonylation of methanol, by-products are formed. One by-product is acetaldehyde. Reduction of acetaldehyde has been described in the art. For example, U.S. Pat. No. 5,756,836 teaches a process for producing a highly purified acetic acid characterized in that the process comprises the step of continuously reacting methanol and/or an aqueous solution of methyl acetate with carbon monoxide in a reactor. A treatment is conducted to limit the concentration of unsaturated compounds in crude acetic acid obtained in the process to 5 wppm or lower, and the resultant crude acetic acid is ozonized. The '836 patent also teaches a process for producing a highly purified acetic acid, characterized by the step of continuously reacting methanol and/or an aqueous solution of methyl acetate with carbon monoxide in a reactor while maintaining the concentration of acetaldehyde in a reaction fluid in the reactor at 1500 wppm or lower. The acetaldehyde concentration is controlled by conducting said reaction at a water content not greater than 10 wt. % and an acetaldehyde concentration of not greater than 1500 wppm to produce a crude acetic acid product mixture; sending the crude acetic acid product mixture to a distillation column to produce a high-boiling point fraction and a low-boiling point fraction; treating the low-boiling point fraction to reduce the content of acetaldehyde therein; and returning the treated low-boiling point fraction to the reaction system.

U.S. Pat. No. 5,625,095 also suggests that acetaldehyde concentration should be reduced. The '095 patent discloses a high purity acetic acid prepared by reacting methanol with carbon monoxide in the presence of a rhodium catalyst, iodide salts, and methyl iodide, wherein an acetaldehyde concentration in the reaction liquid is maintained at 400 wppm or lower. This may be attained by contacting the liquid containing carbonyl impurities with water to separate and remove the carbonyl impurities. After that, the liquid can be returned to the reactor.

U.S. Pat. No. 6,573,403 teaches a process for producing acetic acid which comprises charging reactants methanol, dimethyl ether, methyl acetate or any mixture thereof into a reactor containing: (1) a rhodium carbonylation catalyst, (2) an alkyl iodide or alkyl bromide, and (3) a hydrogenation catalyst, and contacting the reactants with carbon monoxide and hydrogen to produce acetic acid. The '403 patent further teaches that the addition of ruthenium compounds to the carbonylation reaction solution conditions effectively reduces the formation of undesired carbonyl impurities whilst increasing the formation of ethanol, ethyl acetate and ethyl iodide being precursors for the formation of valuable propanoic acid.

Additional methods for removing permanganate reducing compounds (PRC's), such as acetaldehyde, are disclosed in U.S. Pat. Nos. 7,855,306 and 7,683,212. The '306 patent teaches a process for reducing and/or removing permanganate reducing compounds or their precursors from intermediate streams during the formation of acetic acid. In particular, a low boiling overhead vapor stream from a light ends column is subjected to a single distillation to obtain an overhead that is subjected to an extraction to selectively remove and/or reduce PRC's from the process. The '212 patent teaches a method to produce acetic acid by continuously reacting methanol with carbon monoxide in the presence of a rhodium catalyst, an iodide salt, methyl iodide, methyl acetate, and water; and thereby producing acetic acid at a production rate of 11 mol/L·hr or more while keeping the acetaldehyde content of a reaction mixture to 500 wppm or less, in which the reaction is carried out at a carbon monoxide partial pressure in a gaseous phase of a reactor of 1.05 MPa or more and/or at a methyl acetate content of the reaction mixture of 2 percent by weight or more to thereby keep the production rate of acetaldehyde to $\frac{1}{1500}$ or less that of acetic acid. The '212 patent teaches that this method can reduce production of by-products without reducing the reaction rate of acetic acid even at a low water content and a low hydrogen partial pressure in a reaction system.

U.S. Pat. No. 6,303,813 discloses methanol carbonylation methods which substantially reduce the production of carbonyl impurities, particularly acetaldehyde, crotonaldehyde, and 2-ethyl crotonaldehyde, by maintaining a partial pressure of hydrogen between about 0.4 and 4 psia at reaction total pressure of from about 15 to about 40 atmospheres total reaction pressure.

Although the above-described publications focus on suppressing or removing carbonyl impurities such as acetaldehyde and crotonaldehyde from carbonylation reaction systems, little art exists concerning butyl acetate, which can be formed from these impurities. The need therefore exists for improved processes for producing a high purity acetic acid comprising low amounts of butyl acetate.

SUMMARY OF THE INVENTION

In a first embodiment, the present invention is directed to a process for producing an acetic acid product, comprising the steps of continuously carbonylating at least one member selected from the group consisting of methanol, dimethyl ether, and methyl acetate with carbon monoxide in a reactor in the presence of water, a metal catalyst, methyl iodide and a halide salt to form a reaction medium, wherein the carbonylating is carried out at a temperature from 150 to 250° C., a hydrogen partial pressure from 0.3 to 2 atm, and a metal catalyst concentration from 100 to 3000 wppm, based on the weight of the reaction medium, removing acetaldehyde from a stream derived from the reaction medium to form the acetic acid product, and maintaining a butyl acetate concentration in the acetic acid product at 10 wppm or less. The reaction medium may comprise less than 1500 wppm acetaldehyde. The reaction medium may comprise from 0.1 to 3.5 wt. % water. The reaction medium may comprise from 400 to 1500 wppm metal catalyst. In one aspect, the hydrogen partial pressure is from 0.3 to 1.5 atm. In another aspect, the hydrogen partial pressure is from 0.4 to 1.5 atm. The methanol may be introduced into the reactor in a methanol source comprising from 1 to 150 wppm ethanol. The acetic acid product may comprise less than 250 wppm propionic acid. Removing acetaldehyde from a stream derived from the reaction medium may comprise: (a) separating at least a portion of the reaction medium to provide a vapor overhead stream comprising acetic acid and a less volatile catalyst phase; (b) distilling the vapor overhead stream to yield a purified acetic acid product and a first overhead stream comprising methyl iodide, water, acetic acid, methyl acetate, and acetaldehyde; (c) distilling at least a portion of the first overhead stream to form a second overhead stream and a liquid phase residuum, wherein the second overhead stream is enriched with acetaldehyde with respect to the at least a portion of the first overhead stream; and (d) extracting the second overhead stream with water to obtain an aqueous acetaldehyde stream comprising acetaldehyde and a raffinate comprising methyl iodide. The methyl iodide from the raffinate may be returned, directly or indirectly, to the reactor. The process may further comprise condensing and biphasically separating the first overhead stream to form a light liquid phase and a heavy liquid phase, wherein at least a portion of the light liquid phase is returned to the reactor.

In a second embodiment, the present invention is directed to a process for producing acetic acid, comprising: providing a reaction medium comprising acetic acid, methanol, methyl acetate, less than 4 wt. % water, a metal catalyst, methyl iodide and a halide organic salt; removing acetaldehyde from a stream derived from the reaction medium to form the acetic acid product, and maintaining a butyl acetate concentration in the acetic acid product at 10 wppm or less. The butyl acetate concentration may be maintained by removing acetaldehyde from a stream derived from the reaction medium and by adjusting at least one of reaction temperature, hydrogen partial pressure, and metal catalyst concentration in the reaction medium. In one aspect, the hydrogen partial pressure is from 0.3 to 2 atm. In another aspect, the hydrogen partial pressure is at least 0.4 atm. The removing acetaldehyde may comprise: (a) separating at least a portion of the reaction medium to provide a vapor overhead stream comprising acetic acid and a less volatile catalyst phase; (b) distilling the vapor overhead stream to yield a purified acetic acid product and a first overhead stream comprising methyl iodide, water, acetic acid, methyl acetate, and acetaldehyde; (c) distilling at least a portion of the first overhead stream to form a second overhead stream and a liquid phase residuum, wherein the second overhead stream is enriched with acetaldehyde with respect to the at least a portion of the first overhead stream; and (d) extracting the second overhead stream with water to obtain an aqueous acetaldehyde stream comprising acetaldehyde and a raffinate comprising methyl iodide. Methyl iodide from the raffinate may be returned, directly or indirectly, to the reactor. The process may further comprise condensing and biphasically separating the first overhead stream to form a light liquid phase and a heavy liquid phase, wherein the at least a portion of the first overhead stream distilled in step (c) comprises the light liquid phase. The process may further comprise condensing and biphasically separating the first overhead stream to form a light liquid phase and a heavy liquid phase, wherein the at least a portion of the first overhead stream distilled in step (c) comprises the heavy liquid phase. The process acetic acid product may comprise less than 250 wppm propionic acid.

In a third embodiment, the present invention is directed to a process for producing an acetic acid product, comprising the steps of: continuously reacting methanol with carbon monoxide in the presence of a rhodium catalyst, an iodide salt, and methyl iodide to form a reaction medium, wherein the reaction is carried out at a temperature from 100 to 300° C. and a hydrogen partial pressure from 0.3 to 2 atm, wherein the reaction medium comprises from 100 to 3000 wppm rhodium, separating the acetic acid product from the reaction medium; determining the butyl acetate concentration in the acetic acid product; adjusting at least one of the temperature, the hydrogen partial pressure and the rhodium catalyst concentration when the butyl acetate concentration in the acetic acid product is greater than 10 wppm; and removing acetaldehyde from a stream derived from the reaction medium to maintain an acetaldehyde concentration of less than 1500 wppm in the reaction medium.

BRIEF DESCRIPTION OF THE DRAWINGS

The present invention will be better understood in view of the appended non-limiting figures, wherein.

DETAILED DESCRIPTION OF THE INVENTION

I. Introduction

The present invention relates to processes for producing acetic acid, comprising carbonylating at least one member selected from the group consisting of methanol, dimethyl ether and methyl acetate in the presence of a water, a metal catalyst, methyl iodide and a halide salt to form a reaction medium. The carbonylating is carried out at a temperature from 150 to 250° C., a hydrogen partial pressure from 0.3 to 2 atm, and a metal catalyst concentration from 100 to 3000 wppm based on the weight of the reaction medium, while maintaining a butyl acetate concentration in the high purity acetic at 10 wppm or less. Due to the difficulty in removing butyl acetate from acetic acid in a carbonylation purification process, butyl acetate concentration in the acetic acid product is not easily controlled. Butyl acetate is not a PRC, but it is an impurity that can lead to degradation of acetic acid product quality in concentrations above 10 wppm. The butyl acetate concentration in the final high purity acetic acid product is at least partially maintained by removing acetaldehyde from a stream derived from the reaction medium. The butyl acetate concentration in the final high purity acetic acid product may also be maintained by adjusting at least one of the reaction temperature, the hydrogen partial pressure, the metal catalyst concentration, and the water concentration. It has been surprisingly and unexpectedly discovered that by removing acetaldehyde from a stream derived from the reaction medium and by controlling at least one of reaction temperature, hydrogen partial pressure, and metal catalyst concentration in the reaction medium, the amount of butyl acetate in the final acetic acid product can be advantageously maintained at 10 wppm or less. As a consequence of these controls, the amount of propionic acid in the final acetic acid product can be maintained at 250 wppm or less.

Figure 1:
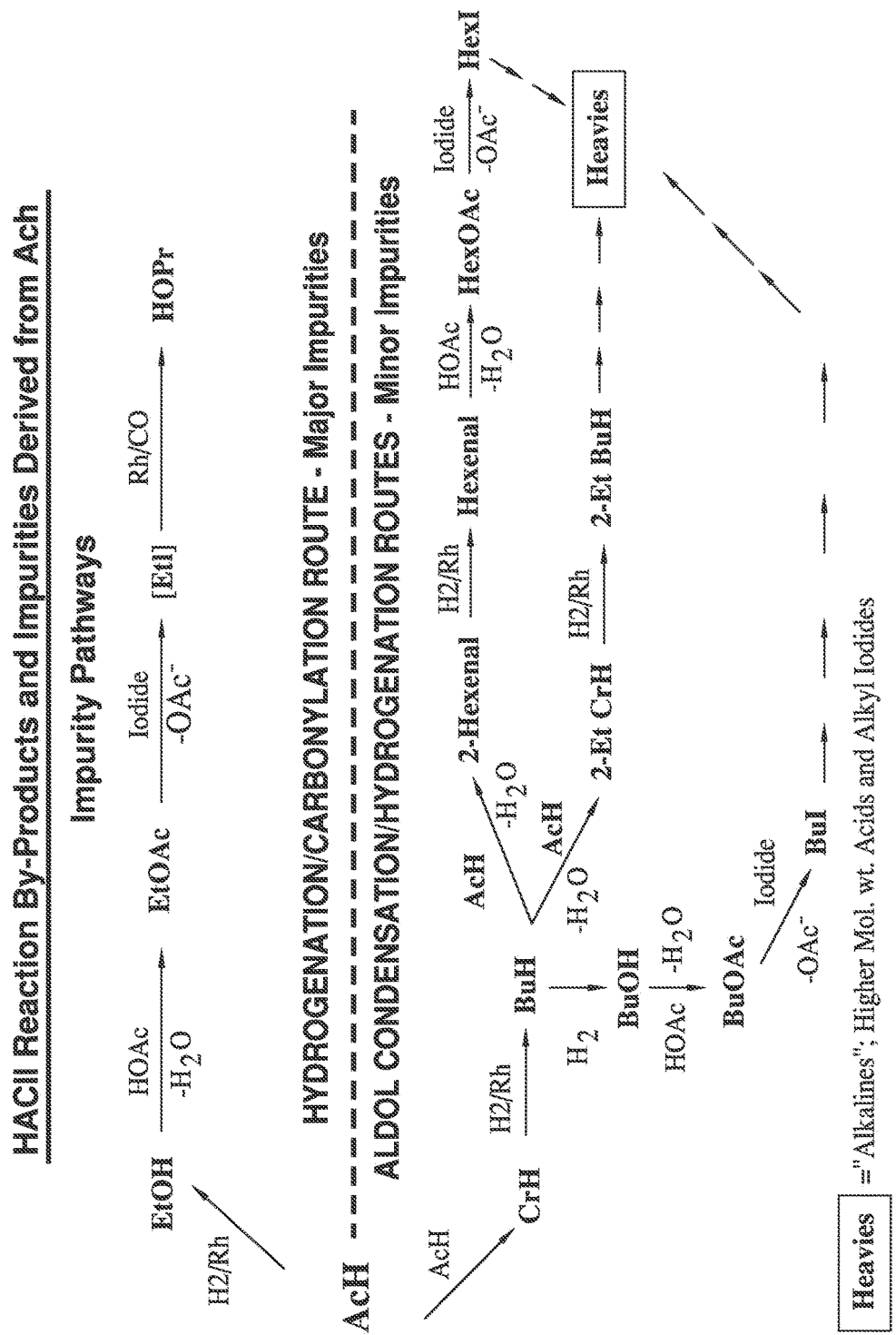
FIG. 1 shows a schematic of acetic acid reaction byproducts and impurities derived from acetaldehyde.

In addition to the carbonylation reaction, several side reactions occur in the reaction medium. Without being bound by theory, FIG. 1 shows various by-products and impurities that may be formed in a carbonylation process by hydrogenation and aldol condensation reactions. When acetaldehyde is present in the reaction medium, the acetaldehyde is converted to crotonaldehyde via an aldol condensation reaction. Crotonaldehyde may then be hydrogenated to butyl aldehyde, which may then be hydrogenated to butanol. Finally, butanol may react with acetic acid to form butyl acetate. In addition to butyl aldehyde being hydrogenated to butanol, butyl aldehyde may react with acetaldehyde to form additional impurities, as shown in FIG. 1. As shown in FIG. 1, acetaldehyde concentration is only one factor affecting butyl acetate concentration in the final acetic acid product. Thus, acetaldehyde concentration in the reaction medium is not an accurate predictor, by itself, of final butyl acetate content and other parameters may be controlled to achieve the desired butyl acetate content in the final acetic acid product.

II. Carbonylation Reaction Step

Figure 2:
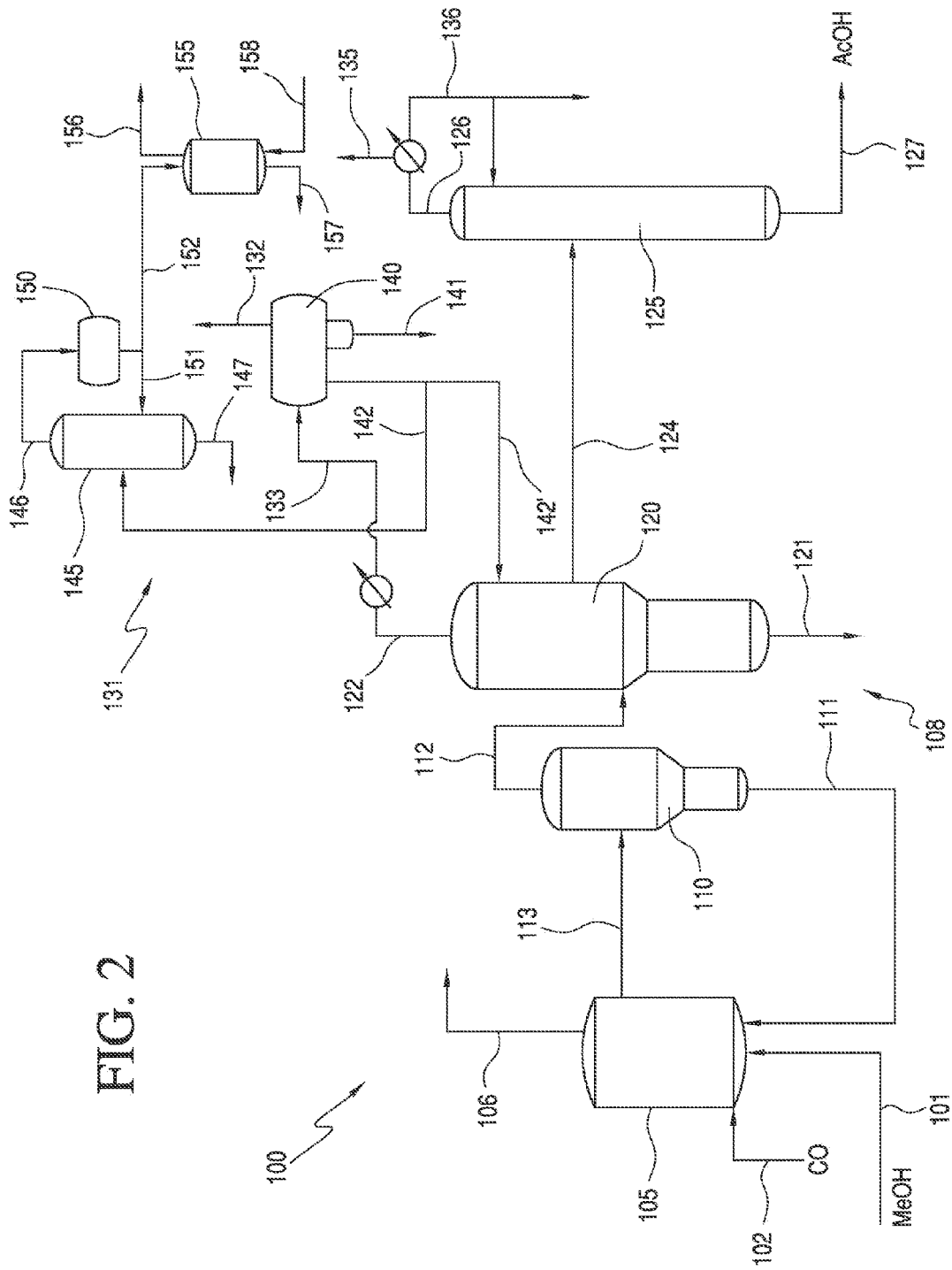
FIG. 2 shows a schematic of an acetic acid production process in accordance with the present invention.

Exemplary reaction and acetic acid recovery system 100 is shown in FIG. 2. As shown, methanol-containing feed stream 101 and carbon monoxide-containing feed stream 102 are directed to liquid phase carbonylation reactor 105, in which the carbonylation reaction occurs to form acetic acid.

Methanol-containing feed stream 101 may comprise at least one member selected from the group consisting of methanol, dimethyl ether, and methyl acetate. Methanol-containing feed stream 101 may be derived in part from a fresh feed or may be recycled from the system. At least some of the methanol and/or reactive derivative thereof will be converted to, and hence be present as, methyl acetate in the liquid medium by esterification reaction with acetic acid.

Typical reaction temperatures for carbonylation will be from 150 to 250° C., with the temperature range of 180 to 225° C. being a preferred range. The carbon monoxide partial pressure in the reactor can vary widely but is typically from 2 to 30 atm, e.g., from 3 to 10 atm. The hydrogen partial pressure in the reactor is typically from 0.3 to 2 atm, e.g., from 0.3 to 1.5 atm, or from 0.4 to 1.5 atm. Because of the partial pressure of by-products and the vapor pressure of the contained liquids, the total reactor pressure will range from 15 to 40 atm. The production rate of acetic acid may be from 5 to 50 mol/L·h, e.g., from 10 to 40 mol/L·h, and preferably 15 to 35 mol/L·h.

Carbonylation reactor 105 is preferably either a mechanically stirred vessel, a vessel with educted or pump-around mixing, or bubble-column type vessel, with or without an agitator, within which the reacting liquid or slurry contents are maintained, preferably automatically, a predetermined level, which preferably remains substantially constant during normal operation. Into carbonylation reactor 105, fresh methanol, carbon monoxide, and sufficient water are continuously introduced as needed to maintain suitable concentrations in the reaction medium.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]$-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, which are incorporated herein by reference in their entirety. The carbonylation of methanol utilizing iridium catalyst is well known and is generally described in U.S. Pat. Nos. 5,942,460, 5,932,764, 5,883,295, 5,877,348, 5,877,347 and 5,696,284, which are incorporated herein by reference in their entirety.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

The components of the reaction medium are maintained within defined limits to ensure sufficient production of acetic acid. The reaction medium contains a concentration of the metal catalyst, e.g. rhodium catalyst, in an amount from 100 to 3000 wppm, e.g., from 400 to 2000 wppm, or from 400 to 1500 wppm as rhodium. The concentration of water in the reaction medium is maintained to be less than 14 wt. %, e.g., from 0.1 wt. % to 14 wt. %, from 0.2 wt. % to 10 wt. % or from 0.25 wt. % to 5 wt. %. Preferably, the reaction is conducted under low water conditions and the reaction medium contains less than 4 wt. % water, e.g., less than 3.5 wt. %, less than 3 wt. %, or less than 2 wt. %. In terms of ranges, the reaction medium contains 0.1 to 3.5 wt. % water, e.g, from 0.1 to 3 wt. % or from 0.5 to 2.8 wt. %. The concentration of methyl iodide in the reaction medium is maintained to be from 1 to 25 wt. %, e.g., from 5 to 20 wt. %, from 4 to 13.9 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 4.1 wt. %. The following amounts are based on the total weight of the reaction medium. The ranges disclosed in this application include the endpoints, subranges and individual values.

The concentration of acetic acid in the reaction medium is generally more than 30 wt. %, e.g. more than 40 wt. % or more than 50 wt. %.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously.

The carbonylation reaction of methanol to acetic acid product may be carried out by contacting the methanol feed with gaseous carbon monoxide bubbled through an acetic acid solvent reaction medium containing the rhodium catalyst, methyl iodide (MeI) promoter, methyl acetate (MeAc), and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, March 2002 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 wppm.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 105 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Stream 105 comprising the liquid reaction medium exits reactor 105.

The acetic acid production system preferably includes separation system 108 employed to recover the acetic acid and recycle metal catalyst, methyl iodide, methyl acetate, and other system components within the process. One or more of the recycle streams may be combined prior to being introduced into the reactor. The separation system also preferably controls water and acetic acid content in the carbonylation reactor, as well as throughout the system, and facilitates permanganate reducing compound ("PRC") removal. PRC's may include acetaldehyde, acetone, methyl ethyl ketone, butylaldehyde, crotonaldehyde, 2-ethyl crotonaldehyde, 2-ethyl butyraldehyde, and the aldol condensation products thereof.

The reaction medium is drawn off from the carbonylation reactor 105 at a rate sufficient to maintain a constant level therein and is provided to flasher 110 via stream 113. The flash separation may be carried out at a temperature from 80° C. to 200° C., under an absolute pressure from 1 to 10 atm. In flasher 110, the reaction medium is separated in a flash separation step to obtain a vapor product stream 112 comprising acetic acid and liquid recycle 111 comprising a catalyst-containing solution.

In addition to acetic acid, vapor product stream 112 also comprises methyl iodide, methyl acetate, water, PRC's. Dissolved gases exiting reactor 105 and entering flasher 110 comprise a portion of the carbon monoxide and may also contain gaseous by-products such as methane, hydrogen, and carbon dioxide. Such dissolved gases exit flasher 110 as part of the vapor product stream 112. In one embodiment, carbon monoxide in gaseous purge stream 106 is fed to the base of flasher 110 to enhance rhodium stability. The catalyst-containing solution in liquid recycle 111 may be predominantly acetic acid and also contain the rhodium and the iodide salt along with lesser quantities of methyl acetate, methyl iodide, and water. The catalyst-containing solution in liquid recycle 111 is recycled to the reactor, as discussed above.

III. Butyl Acetate Concentration in the Final Acetic Acid Product

As described herein, a acetic acid product, preferably a high purity acetic acid product, is formed by the processes of the present invention, preferably having a butyl acetate concentration of 10 wppm or less, e.g., 9 wppm or less, 8 wppm or less, 6 wppm or less, 2 wppm or less or substantially free of butyl acetate, e.g., non-detectable. In terms of ranges, the acetic acid product may have a butyl acetate content from 0 to 10 wppm, e.g., from 0.1 to 9 wppm, from 0.2 to 8 wppm, from 0.3 to 6 wppm, or from 0.5 to 2 wppm. The high purity acetic acid product also preferably has a propionic acid concentration of less than 250 wppm propionic acid, e.g., less than 225 wppm or less than 200 wppm. One variable that may be adjusted to control the butyl acetate concentration of the high purity acetic acid product is the acetaldehyde concentration in the reaction medium. As disclosed herein, butyl acetate is a by-product formed from acetic acid and butanol, which is derived ultimately from acetaldehyde as shown in FIG. 1. Thus, as acetaldehyde concentration is decreased, butyl acetate concentration is generally decreased. Acetaldehyde removal systems are described further herein, including in FIG. 2. Preferably, the acetaldehyde concentration in the reaction medium is maintained at less than 1500 wppm acetaldehyde, e.g., less than 900 wppm, less than 500 wppm, or less than 400 wppm.

The acetaldehyde concentration in the reaction medium may be controlled by removing acetaldehyde from a stream derived from the reaction medium. This includes streams that are intended to be recycled to the reactor and that are derived from the vapor overhead stream, but excludes the acetic acid product stream.

In addition to removing acetaldehyde from a stream derived from the reaction medium, it has now been discovered that butyl acetate concentration in the final acetic acid product may be controlled by adjusting at least one of reaction temperature, hydrogen partial pressure, and metal catalyst concentration in the reaction medium. The reaction temperature may be adjusted within the range of 150 to 250° C., e.g., within 180 to 225° C. Hydrogen partial pressure may be adjusted within the range of 0.3 to 2 atm, e.g., from 0.3 to 1.5 atm, from 0.4 to 1.5 atm, or from 0.3 to 1 atm. In some aspects, the hydrogen partial pressure is at least 0.3 atm, e.g., at least 0.35 atm, at least 0.4 atm or at least 0.5 atm. It is understood that 1 atm is equivalent to approximately 101.33 kPa and 14.70 psi. As hydrogen partial pressure is increased, the water-gas shift reaction of carbon monoxide and water to carbon dioxide and hydrogen is affected since the carbon dioxide component is decreased. Increasing the hydrogen partial pressure also allows for the reduction in temperature, leading to reduced operating costs. Finally, increasing the hydrogen partial pressure improves metal catalyst activity, e.g., rhodium activity, by shifting the reaction equilibria to more rhodium in the active form. However, as hydrogen partial pressure is increased, impurity production is also increased. Thus, hydrogen partial pressure and reaction temperature are balanced to achieve satisfactory yields, costs, and impurity concentrations. The hydrogen partial pressure may be adjusted by modifying the amount of hydrogen in the carbon monoxide source or by increasing reactor vent flows.

Based on the reaction mechanisms disclosed in FIG. 1, the concentration of propionic acid may be affected by the concentration butyl acetate in the acetic acid product. The concentration of propionic acid may be affected by other variables, including the concentration of acetaldehyde, ethanol content in the methanol source, hydrogen partial pressure, hydrogen content in the carbon monoxide source and reaction pressure. Ethanol may be present as an impurity in the methanol source, which may comprise from 1 to 150 wppm ethanol, e.g., from 1 to 100 wppm, from 1 to 50 wppm or from 1 to 25 wppm. The ethanol concentration in the methanol source may vary. Optionally, the methanol source is purified to increase methanol content and reduce ethanol content prior to feeding to the carbonylation reactor. Therefore, the ethanol concentration in the methanol source may be less than 1 wppm, e.g., free of ethanol.

IV. Recovery of Acetic Acid

The distillation and recovery of acetic acid is not particularly limited for the purposes of the present invention. In contrast to previous methods that recover acetic acid from the vapor product stream, the present invention recovers acetic acid from both the vapor product stream and a liquid stream condensed from the vapor product stream that is enriched in acetic acid.

As shown in FIG. 2, vapor product stream 112 is directed to a first column 120, also referred to as a light ends column. Distillation yields a low-boiling overhead vapor stream 122, a purified acetic acid product that preferably is removed via a side stream 124, and a high boiling residue stream 121. In one embodiment, low-boiling overhead vapor stream 122 comprises from 40 to 80 wt. % water, methyl acetate, methyl iodide, and carbonyl impurities including acetaldehyde. Side stream 124 may comprise from 85 to 98 wt. % acetic acid, from 1 to 5 wt. % water, from 0.1 to 5 wt. % methyl iodide, and from 0.1 to 5 wt. % methyl acetate. Acetic acid removed via side stream 124 preferably is subjected to further purification, such as in a second column 125, also referred to as a drying column, and separates side stream 124 into overhead stream 126 comprised primarily of water and bottoms stream 127 comprised primarily of acetic acid, e.g., the acetic acid product. Propionic acid in column 125 is concentrated with the acetic acid product in an amount of less than 250 wppm and is not removed from the acetic acid product. In some embodiments, the acetic acid product may be taken as a side stream (not shown) from column 125. Advantageously, this avoids the need for an additional separation step for removing propionic acid from acetic acid. For example, no heavy ends removal is needed.

Overhead stream 126 may comprise 50 to 75 wt. % water. Methyl acetate and methyl iodide are also removed from the side stream and concentrated in the overhead stream. Drying column bottoms stream 127 preferably comprises acetic acid. In preferred embodiments, drying column bottoms stream 127 comprises acetic acid in an amount greater than 90 wt. %, e.g., greater than 95 wt. % or greater than 98 wt. % and comprises less than 250 wppm propionic acid. Drying column bottoms stream 127 may be further processed, e.g. by passing through an ion exchange resin, prior to being stored or transported for commercial use.

Low-boiling overhead vapor stream 122 separated from first column 120 contains a reaction component, such as methyl iodide, methyl acetate, and water, and it is preferable to retain these reaction components within the process. Low-boiling overhead vapor stream 122 is condensed in a heat exchanger into stream 133. At least a portion of stream 133 may be directed to a PRC's removal unit 131, discussed herein. Optionally, a portion of stream 133 is recycled to reactor 105 and/or refluxed first column 120. Similarly, overhead stream 126 from second column 125 contains a reaction component, such as methyl iodide, methyl acetate, and water, and it is preferable to retain these reaction components within the process. Overhead stream 126 is condensed in a heat exchanger into stream 136, which is recycled to reactor 105 and/or refluxed second column 125. An offgas component may be vented via line 135 from condensed low-boiling overhead vapor stream 126. Similar to the condensed low-boiling overhead vapor stream in stream 133, condensed overhead stream in stream 136 may also be separated into an aqueous phase and an organic phase, and these phases may be recycled or refluxed as needed to maintain the concentrations in the reaction medium.

To recover residue liquids from the vent stream, in particular lines 106, 132, 135, and 122, these lines may be fed to a scrubber that operates with cooled methanol and/or acetic acid to remove methyl acetate and methyl iodide. A suitable scrubber is described in U.S. Pat. No. 8,318,977, which is incorporated herein by reference in its entirety.

The distillation columns of the present invention may be conventional distillation column, e.g., a plate column, a packed column, and others. The material of the distillation column is not limited and may include a glass, a metal, a ceramic, or other suitable material can be used. For a plate column, the theoretical number of plates may depend on the component to be separated, and may include up to 50 plates, e.g., from 5 to 50, or from 7 to 35.

V. PRC Removal System (PRS)

The PRS may contain a single extraction step or may include multiple extraction stages, as described for example in U.S. Pat. No. 7,223,886 and optionally including multistage countercurrent extraction. According to various embodiments, one or more streams derived from either or both (i) the PRS distillation column and/or (ii) the PRS extraction stage, for example, may be returned to the system, e.g., either or both (i) the light ends removal column and/or (ii) the drying column of the separation system for the acetic acid production system. For example, a first portion, e.g., an aliquot portion, of a bottoms stream from a PRS column may be directed to light ends column 120 for further processing, or a second portion, e.g., an aliquot portion, of a bottoms stream from a PRS column may be directed to drying column 125, preferably the upper portion of drying column 125, for further processing. As another example, a raffinate from a PRS extraction unit, notably containing methyl iodide, may be returned to the system, e.g., light ends column or drying column or the raffinate may be added directly to decanter 140 and/or may be returned to reactor 105.

For purposes of the present specification and claims, the overhead streams and overhead decanters of the light ends removal column and the drying column are considered to be part of the light ends removal column and of the drying column.

As indicated above, either phase of the low-boiling overhead vapor stream 133 may be subsequently processed to remove PRC's. Thus, either phase of stream 133 may be referred to as a stream derived from the reaction medium.

For purposes of the present specification, it should be understood that the term "aliquot portion" refers to both: (i) a portion of a parent stream that has the same composition as the parent stream from which it is derived, and (ii) a stream comprising a portion of a parent stream that has the same composition as the parent stream from which it is derived and one or more additional streams that have been combined therewith. Thus, directing a return stream comprising an aliquot portion of a PRS distillation bottoms stream to the light ends column encompasses the direct transfer of a portion of the PRS distillation bottoms stream to the light ends column as well as the transfer of a derivative stream comprising (i) a portion of the PRS distillation bottoms stream and (ii) one or more additional streams that are combined therewith prior to introduction into the light ends column. An "aliquot portion" would not include, for example, streams formed in a distillation step or a phase separation step, which would not be compositionally the same as the parent stream from which they are derived nor derived from such a stream.

One of ordinary skill in the art having the benefit of this disclosure can design and operate a PRS distillation column to achieve the desired results. Accordingly, the practice of this process is not necessarily limited to specific characteristic of a particular distillation column or the operation characteristics thereof, such as the total number of stages, the feed point, reflux ratio, feed temperature, reflux temperature, column temperature profile, and the like.

In some cases, it may be advantageous to remove PRC's, primarily aldehydes such as acetaldehyde, from a low-boiling overhead vapor stream of a light ends distillation column, more preferably from the condensed light phase of a low-boiling overhead vapor stream 133 from light ends distillation column 120.

One or more of the streams from PRS 131 may be returned to the system, e.g., recycled, either directly or indirectly. The PRS preferably includes at least one distillation column and at least one extraction column to reduce and/or remove PRCs. US Patent Publication No. 2011/0288333, which is hereby incorporated by reference, describes various PRS embodiments that may be employed with the present process.

In one embodiment, as shown in FIG. 2, PRS 131 comprises a column 145, an accumulator 150, and an extractor 155. At least a portion of low-boiling overhead vapor stream 133 is directed to decanter 140 to form a heavy phase stream 141, and a light phase 142. Optionally, a portion of stream 142 is returned to column 120 via stream 142'. Additionally, a portion of heavy phase 141 may be returned to reactor 105. Optionally, a slip stream (not shown), e.g., from 5 to 40 vol. % or from 5 to 20 vol. % of heavy phase 141 is directed to PRS 131. An offgas component may be vented via line 132 from decanter 140.

At least a portion of light phase 142 is directed to column 145 to form a vapor overhead stream 146 and a bottom process stream 147 comprising water, methyl acetate, methanol, and mixtures thereof. Vapor overhead stream 146 is passed through a condenser and collected in accumulator 150. A portion of the condensed vapor overhead stream may be returned to column 145 via line 151. Another portion of the condensed vapor overhead stream is directed to extractor 155 via line 152 to form waste stream 156 comprising at least one PRC, e.g., acetaldehyde, and process stream 157 comprising methyl iodide. An aqueous stream may be provided to extractor 155 via line 158 at a location to obtain a countercurrent flow.

Dimethyl ether ("DME") may be present in the PRS in amount sufficient to reduce the solubility of methyl iodide in the aqueous extracted phase. Reducing the amount of methyl iodide in the aqueous extracted phase reduces losses of methyl iodide into waste stream 156. In some embodiments, this may allow multiple extractions as described in U.S. Pat. Nos. 7,223,886, and 8,076,507, the entireties of which are herein incorporated by reference. The amount of DME may vary depending on the methyl iodide concentrations, and in some embodiments, the amount of DME may range from 3 to 9 wt. %, e.g. from 4 to 8 wt. %. DME may be present in the PRS, formed in the PRS by adding water to the PRS (generally by adding water to column 145) or added to the PRS (generally by adding DME upstream of extractor 155).

VI. Guard Bed

Carboxylic acid streams, e.g., acetic acid streams, that are contaminated with a halides and/or corrosion metals may be contacted with an ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615,806; 5,653,853; 5,731,252; and 6,225,498, which are hereby incorporated by reference in their entireties. Generally, a contaminated liquid carboxylic acid stream is contacted with the inventive ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

The pressure during the contacting step is limited only by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) and 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column. Additionally or alternatively, the guard be may be configured after a heavy ends removal column or finishing column. Preferably the guard bed is configured in a position wherein the temperature acetic acid product stream is low, e.g., less than 120° C. or less than 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in one embodiment the purified acetic acid product in bottoms stream 127 is contacted with a guard bed when total iodide concentration of the purified acetic acid product is less than 1 wppm. Total iodide concentration includes iodide from both organic, $C_1$ to $C_{14}$ alkyl iodides, and inorganic sources, such as hydrogen iodide. A purified acetic acid composition is obtained as a result of the guard bed treatment. The purified acetic acid composition, in one embodiment, comprises less than 100 wppb, iodides, e.g., less than 90 wppb, less than 50 wppb, or less than 25 wppb. In one embodiment, the purified acetic acid composition comprises less than 100 wppb corrosion metals, e.g., less than 750 wppb, less than 500 wppb, or less than 250 wppb. In terms of ranges, the purified acetic acid composition may comprise from 0 to 100 wppb iodides, e.g., from 1 to 50 wppb; and/or from 0 to 1000 wppb corrosion metals, e.g., from 1 to 500 wppb. In other embodiments, the guard bed removes at least 25 wt % of the iodides from the crude acetic acid product, e.g., at least 50 wt % or at least 75 wt %. In one embodiment, the guard bed removes at least 25 wt % of the corrosion metals from the crude acetic acid product, e.g., at least 50 wt % or at least 75 wt %.

VII. Examples

The present invention will be better understood in view of the following non-limiting examples.

Example 1

Figure 3:
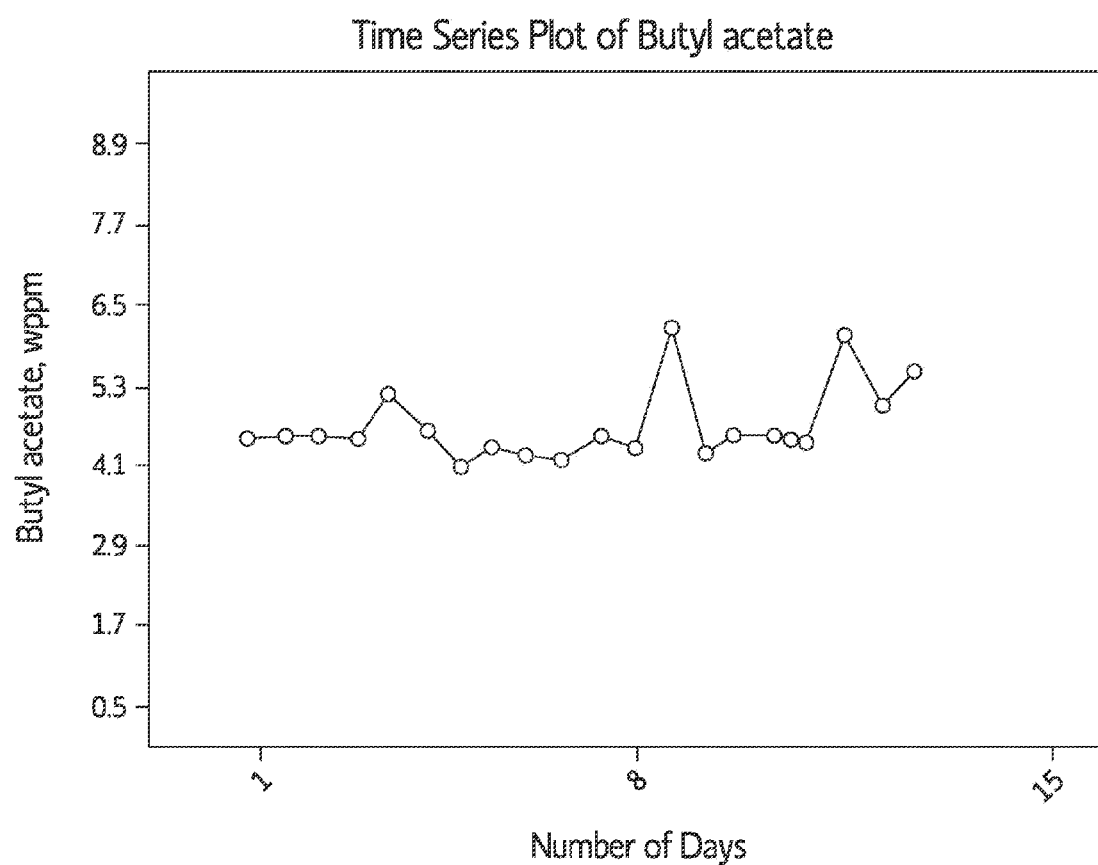
FIG. 3 shows a time series plot of butyl acetate in a final acetic acid product in accordance with the present invention.

A final acetic acid product was prepared as follows. The reaction medium contained 10.8 wt. % methyl iodide, 2.5 wt. % methyl acetate, 4.1 wt. % water, 657 wppm rhodium and 8.4 wt. % lithium iodide. The reaction temperature was 191.8° C. The hydrogen partial pressure was 0.46 atm. The reaction medium was flashed and then separated in a light ends column, PRS, and drying column as described herein. The concentration of butyl acetate in the final acetic acid product was measured over time. The results are shown in FIG. 3. Butyl acetate concentration was consistently below 8 wppm in the final acetic acid product.

Example 2

Figure 4:
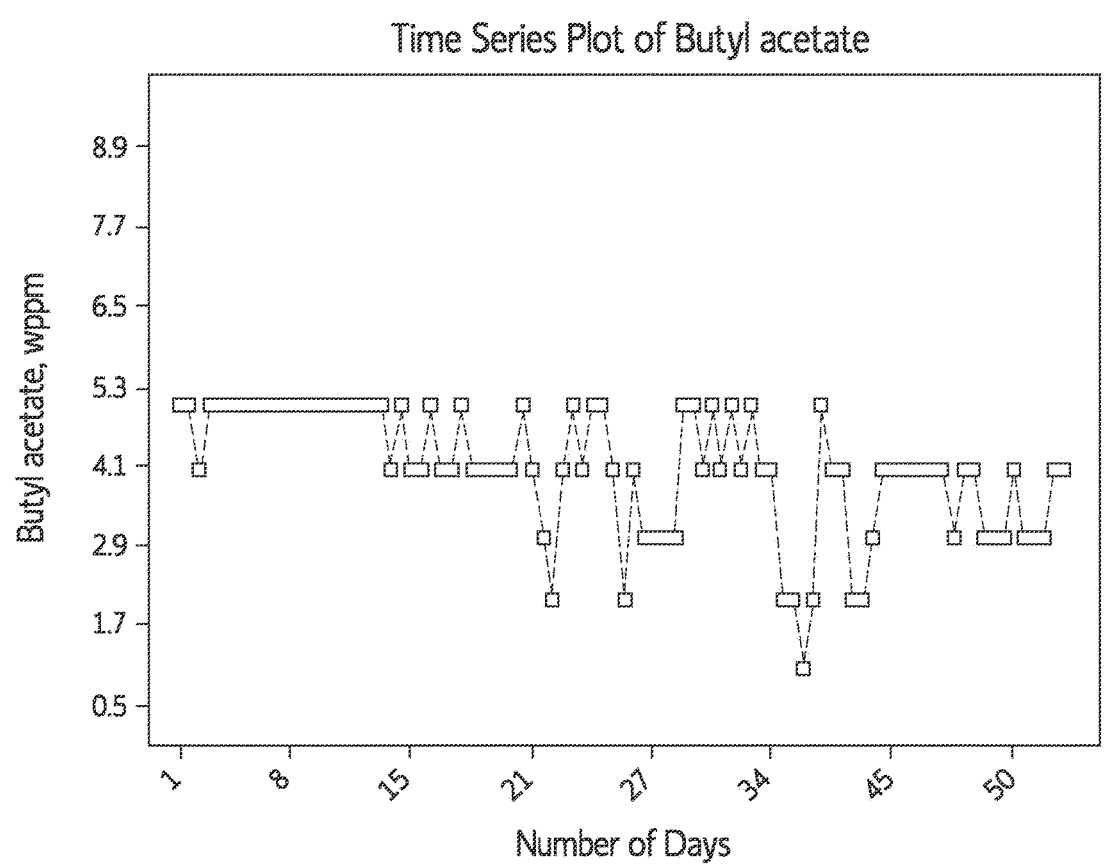
FIG. 4 shows a another time series plot of butyl acetate in a final acetic acid product in accordance with the present invention.

A final acetic acid product was prepared as in Example 1, except that the hydrogen partial pressure was 0.30 atm. The concentration of butyl acetate in the final acetic acid product was measured over time. The results are shown in FIG. 4. Butyl acetate concentration was consistently below 6 wppm in the final acetic acid product.

Example 3

Figure 5:
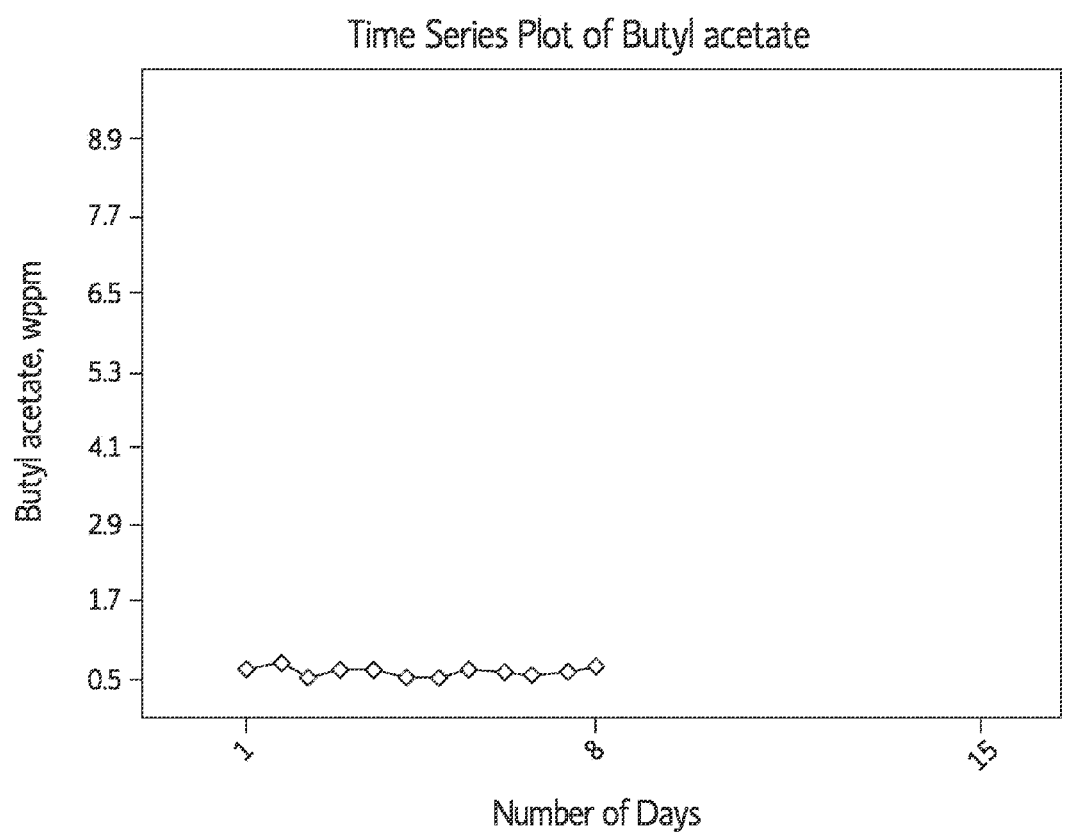
FIG. 5 shows yet another time series plot of butyl acetate in a final acetic acid product in accordance with the present invention.

A final acetic acid product was prepared as in Example 1, except that the hydrogen partial pressure was 0.61 atm. The concentration of butyl acetate in the final acetic acid product was measured over time. The results are shown in FIG. 5. Butyl acetate concentration was consistently below 2 wppm in the final acetic acid product.

Example 4

A final acetic acid product was prepared as in Example 1, except that the reaction medium contained approximately 7 wt. % methyl iodide, approximately 2 wt. % methyl acetate, approximately 2 wt. % water, approximately 1500 wppm rhodium and approximately 9 wt. % to 10 wt. % lithium iodide. The reaction temperature was approximately 200° C. The hydrogen partial pressure was 0.44 atm. Butyl acetate concentration was consistently below 10 wppm in the final acetic acid product.

Comparative Example A

As shown in Example 3 of U.S. Pat. No. 6,303,813, a final acetic acid product was prepared as follows. The reaction medium contained 10.8 wt. % methyl iodide, 2.5 wt. % methyl acetate, 4.1 wt. % water, 657 wppm rhodium and 8.4 wt. % lithium iodide. The reaction temperature was 191.8° C. The hydrogen partial pressure was 0.46 atm. The reaction medium was flashed and then separated in a light ends column, and drying column as described herein. No PRS was used. The concentration of butyl acetate in the final acetic acid product 13 wppm.

Comparative Example B

As shown in Example 4 of U.S. Pat. No. 6,303,813, a final acetic acid product was prepared as follows. The reaction medium contained 10.8 wt. % methyl iodide, 2.5 wt. % methyl acetate, 4.1 wt. % water, 657 wppm rhodium and 8.4 wt. % lithium iodide. The reaction temperature was 191.8° C. The hydrogen partial pressure was 0.30 atm. The reaction medium was flashed and then separated in a light ends column, and drying column as described herein. No PRS was used. The concentration of butyl acetate in the final acetic acid product 16 wppm.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing an acetic acid product comprising the steps of
   carbonylating at least one member selected from the group consisting of methanol, dimethyl ether, and methyl acetate with carbon monoxide in a reaction medium, wherein the carbonylating is carried out at a temperature from 150 to 250° C., a hydrogen partial pressure from 0.3 to 2 atm, and a rhodium catalyst concentration from 100 to 3000 wppm, based on the weight of the reaction medium,
   separating at least a portion of the reaction medium to provide a vapor overhead stream comprising acetic acid and a less volatile catalyst phase;
   distilling at least a portion of the vapor overhead stream to yield a purified acetic acid product and a first overhead stream comprising methyl iodide, water, methyl acetate, and acetaldehyde;
   condensing and biphasically separating the first overhead stream to form a light liquid phase and a heavy liquid phase,
   distilling at least a portion of the heavy liquid phase to form a second overhead stream and a liquid phase residuum;
   extracting the second overhead stream with water to obtain an aqueous acetaldehyde stream comprising acetaldehyde and a raffinate comprising methyl iodide, and
   separating the purified acetic acid product to obtain the acetic acid product, wherein the acetic acid product comprises a butyl acetate concentration of 10 wppm or less.

2. The process of claim 1, wherein the butyl acetate concentration in the acetic acid product is from 0.1 to 9 wppm.

3. The process of claim 1, wherein the butyl acetate concentration in the acetic acid product is from 0.2 to 8 wppm.

4. The process of claim 1, wherein the methanol is introduced into the reactor is a methanol source comprising from 1 to 150 wppm ethanol.

5. The process of claim 1, wherein the acetic acid product comprises less than 250 wppm propionic acid.

6. The process of claim 1, wherein the raffinate is recycled to the reaction medium.

* * * * *